United States Patent [19]
Lee

[11] Patent Number: 5,443,481
[45] Date of Patent: Aug. 22, 1995

[54] METHODS AND DEVICE FOR PERCUTANEOUS SEALING OF ARTERIAL PUNCTURE SITES

[76] Inventor: Benjamin I. Lee, 4911 Van Ness St. NW., Washington, D.C. 20016

[21] Appl. No.: 41,573

[22] Filed: Apr. 5, 1993

Related U.S. Application Data

[63] Continuation-in-part of Ser. No. 918,614, Jul. 27, 1992, Pat. No. 5,292,332.

[51] Int. Cl.⁶ ............... A61B 17/04; A61M 29/00; A61M 39/00
[52] U.S. Cl. .................... 606/213; 606/214; 604/15; 604/49; 604/285; 604/54; 604/96
[58] Field of Search ................ 606/213–215, 606/216; 604/13, 15, 49, 51, 285–288, 54, 96

[56] References Cited

U.S. PATENT DOCUMENTS

| | | | |
|---|---|---|---|
| 4,744,364 | 5/1988 | Kensey . | |
| 4,793,351 | 12/1988 | Landman et al. | 604/99 |
| 4,892,519 | 1/1990 | Songer et al. | 604/96 |
| 4,900,303 | 2/1990 | Lemelson | 604/54 |
| 4,994,033 | 2/1991 | Shockey et al. | 604/96 |
| 5,049,132 | 9/1991 | Shaffer et al. | 604/96 |
| 5,129,882 | 7/1992 | Weldon et al. | 604/96 |

FOREIGN PATENT DOCUMENTS 0476178 3/1992 European Pat. Off. .

*Primary Examiner*—Gary Jackson
*Attorney, Agent, or Firm*—Cushman, Darby & Cushman

[57] ABSTRACT

A method is provided for closing a puncture in a wall of an artery made for the purpose of moving an elongated cardiovascular catheter into the artery. The method includes the steps of withdrawing the cardiovascular catheter from the artery while ensuring that the location of the puncture remains identified, and introducing a thrombogenic, hemostatic material so as to contact the wall of the artery at the puncture location, enabling the material to precipitate clot formation and seal the puncture. A device is also provided to employ the method.

46 Claims, 4 Drawing Sheets

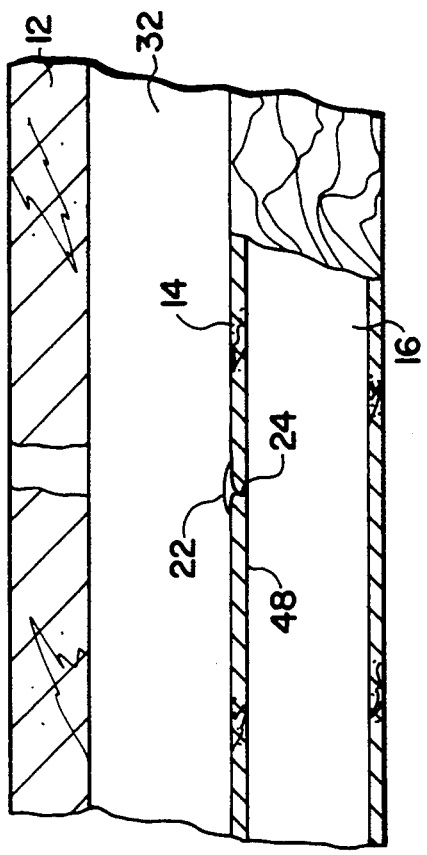
*FIG. 4*
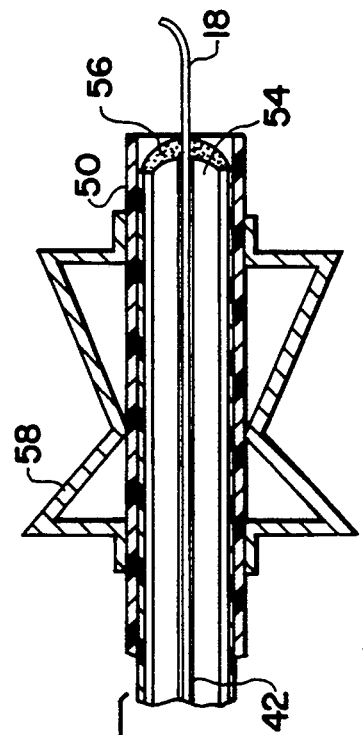
*FIG. 5*
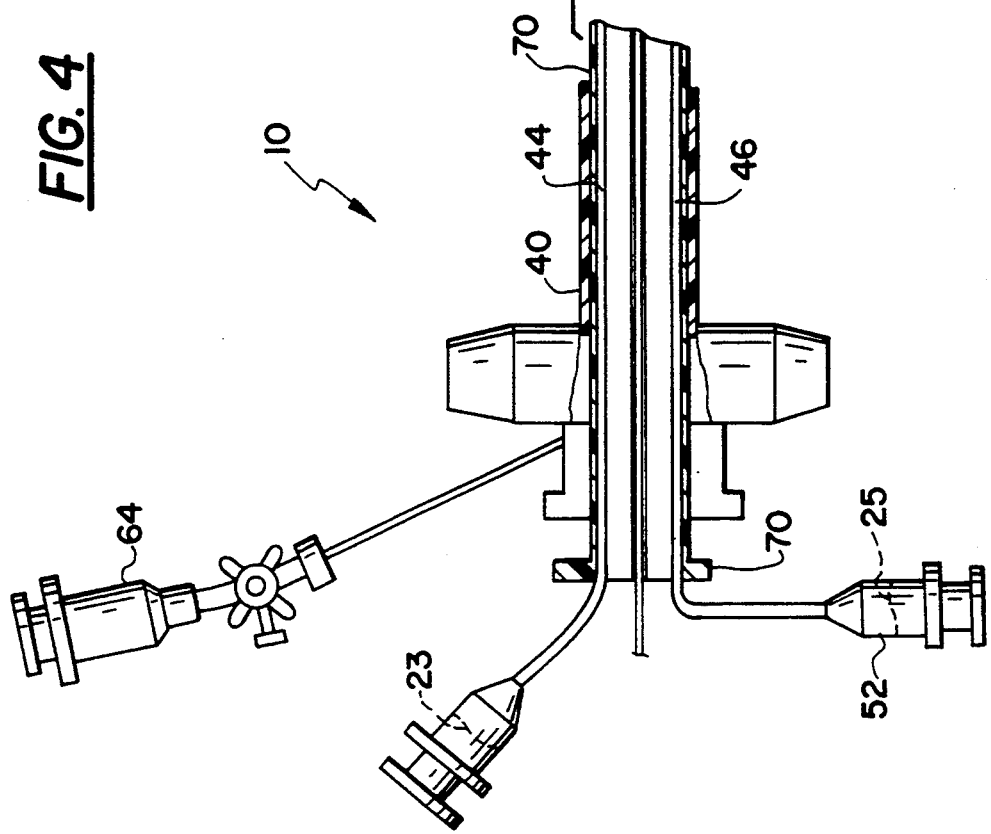

METHODS AND DEVICE FOR PERCUTANEOUS SEALING OF ARTERIAL PUNCTURE SITES

This is a continuation-in-part of application Ser. No. 07/918,614 filed Jul. 27, 1992, now U.S. Pat. No. 5,292,332, the disclosure of which is incorporated herein by this reference.

BACKGROUND OF THE INVENTION

1. Field of the Invention

This invention relates to medical devices and more particularly to a method for percutaneously sealing a puncture in an artery without the need for prolonged manual pressure and without impeding blood flow within the lumen of the artery. A device is also provided to employ the sealing method.

2. Description of the Related Art

Many therapeutic procedures, especially those pertaining to the treatment of atherosclerotic coronary artery and peripheral vascular disease involve percutaneous entry into blood vessels using catheters, guide wires and other devices passed through vascular sheaths. Once the procedure is terminated and the catheters and sheaths removed, adequate hemostasis usually requires direct manual pressure over the arterial puncture site for a duration of 20 to 40 minutes, following which, the patient must remain immobile for an additional 2 to 6 hours. Patient motion during this time and/or inadequate hemostasis may result in serious bleeding complications such as hematoma or pseudoaneurysm formation, which may require surgical repair.

With the increasing utilization of outpatient catheterization procedures, aggressive anticoagulation regimens and larger intraluminal devices, an effective, simple and rapid method of arterial puncture site hemostasis would decrease hospital costs by the more efficient utilization of health care personnel and by shortening the length of hospital stay.

Conventional devices have been developed to close a puncture in a blood vessel, duct or lumen without the need to apply prolonged, direct manual pressure thereto. For example, U.S. Pat. Nos. 4,852,586; 4,890,612; and 4,744,364 to Kensey disclose hemostatic plug devices which are inserted through an arterial sheath into the lumen of the artery prior to removal of the sheath. These plug devices are then pulled back into the arterial puncture site by an attached suture to mechanically occlude the puncture site as the arterial sheath is removed. The plug devices are made of bioabsorbable material and have an enlarged head portion which, when pulled back, substantially seals the luminal surface of the puncture site. However, such devices present numerous disadvantages. There is a potential for the intraluminal head portion of the device to occlude blood flow or cause thrombosis in vessels whose luminal diameter is severely narrowed, since the plug must enter the puncture. In addition, there is a potential for the intraluminal portion of the device to embolize distally as it is bio-degraded.

European Patent Application No. 476,178A1 discloses a device for placing styptic material on perforated blood vessels. The device uses a guide wire to locate the puncture site. A dilator is pushed along the guide wire. A tube is guided along the dilator to the puncture site., The dilator and guide wire are then removed from the tube. A mechanical plug is then pushed through the tube to block the puncture site. However, since the guide wire is removed prior to inserting the plug, it cannot be assured that the plug is in a position so as to properly block the puncture site. Further, since a mechanical plug is utilized, care must be exercised when delivering the plug so that it does not enter, and thus block the vessel.

A need therefore exists to provide a method for closing a puncture in a lumen by placing a thrombogenic, hemostatic, bioabsorbable and biocompatible material on the outer surface of the wall of the lumen at the puncture site to chemically precipitate clot formation and thus, seal the puncture. A need also exists to assure that blood flow in vessels of narrow luminal diameters is not occluded by the introduction of the thrombogenic, hemostatic material.

SUMMARY OF THE INVENTION

An object of the present invention is to fulfill the need referred to above. In accordance with the principles of the present invention, this objective is obtained by providing a method for closing a puncture in a wall of an artery made for the purpose of moving an elongated cardiovascular catheter into the artery. The method includes the steps of withdrawing the cardiovascular catheter from the artery while ensuring that the location of the puncture remains identified, and introducing a thrombogenic, hemostatic material so as to contact the wall of the artery at the puncture location, enabling the material to precipitate clot formation and seal the puncture.

In accordance with a further aspect of the invention a hemostatic device is provided to deliver a thrombogenic, hemostatic material to the vessel puncture to precipitate clotting at the puncture. In accordance with the principles of the present invention, this object is achieved by providing a device which includes an elongated member having a distal end, the elongated member is sized to be fitted through an incision so that the distal end is disposed near the puncture in the artery, and structure for delivering a thrombogenic, hemostatic material to the distal end. The material precipitates formation of a clot upon contact with the wall of the artery at the puncture to seal the puncture.

These and other objects of the present invention will become apparent during the course of the following detailed description and appended claims.

The invention may be best understood with reference to the accompanying drawings wherein illustrative embodiments are shown.

BRIEF DESCRIPTION OF THE DRAWINGS

FIG. 4 is a side elevational view in partial section of the arterial wall with hemostatic device and the thrombogenic, hemostatic material in a position producing hemostasis of the percutaneous puncture site; and FIG. 5 is a side elevational view in partial section of a hemostatic device provided in accordance with a second embodiment of the present invention.

DETAILED DESCRIPTION OF THE PRESENTLY PREFERRED EXEMPLARY EMBODIMENTS

Figure 1:
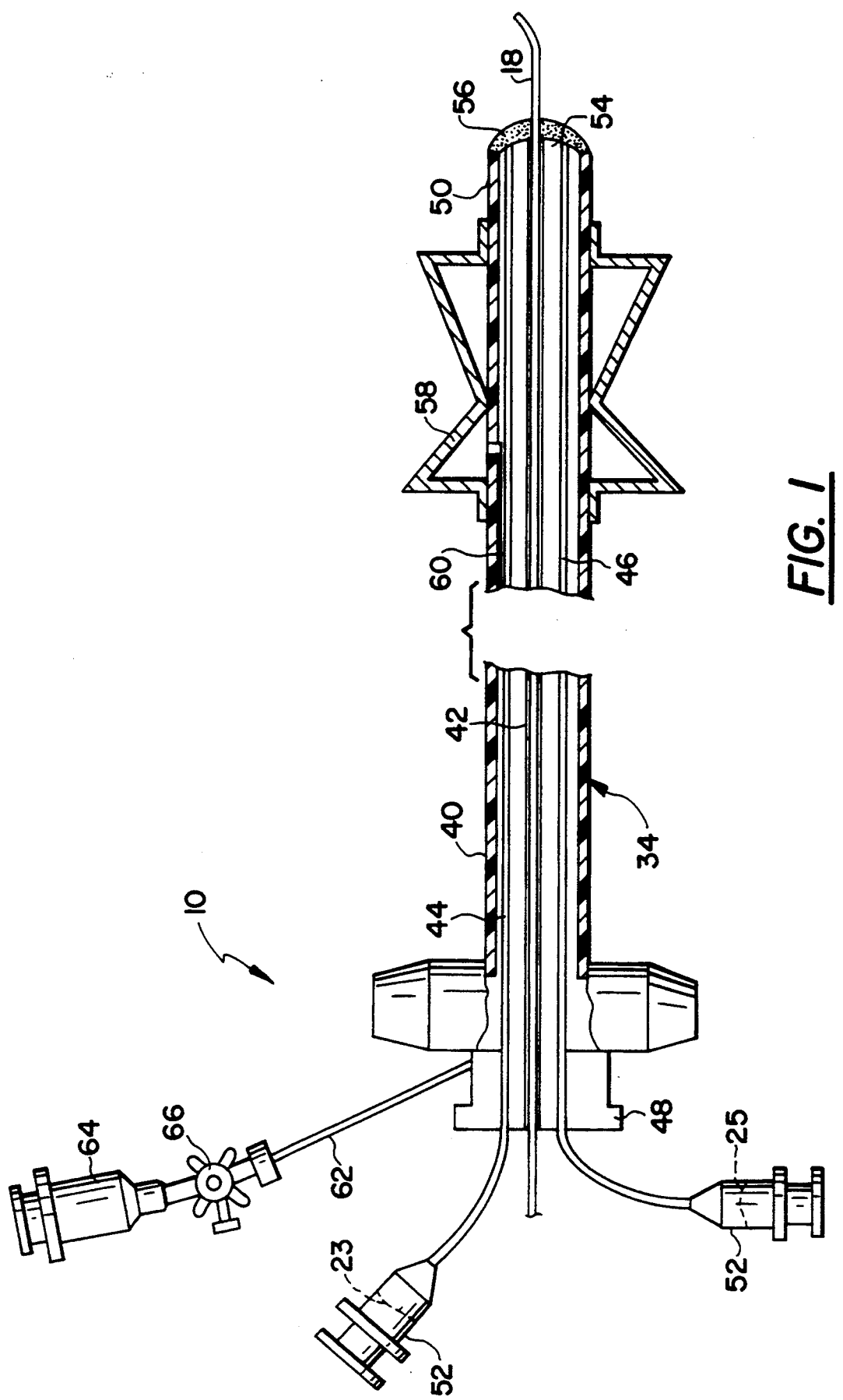
FIG. 1 is a side elevation view partially in section of the hemostatic device provided in accordance with the first embodiment of the present invention.

Referring now in to the drawings, a device, generally indicated at 10, is shown in FIG. 1, which embodies the principles of the present invention. The device 10 may be utilized for effecting hemostasis and closure of a puncture or other openings in a blood vessel, duct or lumen in a living being. This device has particular utility when used in connection with intravascular procedures such as angiography, balloon angioplasty, intraaortic balloon pumping and other types of percutaneous intravascular or intracardiac interventions. A brief description of a conventional percutaneous transcatheter cardiovascular procedure e.g., coronary angiography, percutaneous transluminal angioplasty, is given with reference to FIG. 2, to best appreciate the features of the present invention.

In such a conventional procedure, an angiographic needle such as a Seldinger or Argon needle (not shown) is inserted percutaneously through the skin 12, into an artery, such as the femoral artery 14. The angiographic needle with its tip disposed within the arterial lumen 16 is held while the flexible end of an angiographic guide wire 18 is advanced through the needle into the arterial lumen 16. Once the guide wire is felt to be easily movable within the arterial lumen, the angiographic needle is withdrawn leaving the guide wire in place. A conventional arterial sheath 20 and arterial dilator (not shown) are threaded over the proximal end of the guide wire 18 and advanced over the guide wire through the skin and arterial wall into the arterial lumen 16. The guide wire and dilator are then removed leaving the arterial sheath in place. Angiographic catheters or other intraluminal devices (not shown) are then passed through the arterial sheath 20 and advanced within the artery to the target site by passage over the guide wire. Once the angiographic or angioplasty procedure is completed, the catheters and guide wires are removed, leaving the arterial sheath in place. Finally, the arterial sheath is removed, which then, conventionally requires the physician or other trained medical personnel to apply manual pressure to the puncture site until hemostasis has been achieved.

The device 10 and method of the present invention produce hemostasis and closure of arterial puncture sites by percutaneous means, without necessitating prolonged manual arterial compression.

In accordance with the invention, hemostasis is effected by delivering a thrombogenic, hemostatic material, generally indicated at 22, to the puncture site to promote clotting at the site. The thrombogenic, hemostatic material may include many bioabsorbable and biocompatible materials such as gelatin, blood and tissue components including collagen, blood coagulation factors, blood proteins, fibrinogen, fibrin, thrombin, epsilon aminocaproic acid, autologous blood clots and subcutaneous tissue and other similar materials which promote blood clotting. However, it is preferable that the material be fibrin glue, which may be produced by admixture of two solutions, one of which contains sodium citrate and autologous patient blood, the second of which contains bovine thrombin and aminocaproic acid in water.

It can be appreciated that the material 22 can be delivered to the puncture site in various manners. For example, the two solutions may be mixed remote from the puncture site to form the fibrin glue and then be delivered to the puncture site. Thus, the pre-mixed fibrin glue can be delivered, for example, on the end of an elongated member and deposited at the puncture site, or be delivered by ejecting the fibrin glue from a tubular member once the tubular member is disposed at the puncture site. However, in the preferred method of delivering the material 22 to the puncture site, the two solutions are most preferably in liquid form and have viscosities enabling them to flow easily to the puncture site and thereafter intermix to form the thrombogenic, hemostatic material 22. The material 22 has a greater viscosity than the liquid solutions, enabling the material to remain substantially in its deposited position, as will become more apparent below.

A delivery catheter is provided for delivering the material 22 to the puncture site. In a first embodiment of the invention as shown in FIG. 1, the delivery catheter 34 comprises a hollow tubular member 40. The tubular member 40 is preferably constructed of firm yet flexible material such as PET, polyvinyl chloride or the like. In the illustrated embodiment, the outer diameter of the tubular body is 8 French or less, which enables the tubular body to easily pass through the arterial sheath 20. The tubular member 40 includes a guide wire port 42 therethrough which extends along the longitudinal axis of the tubular body, for housing guide wire 18 therein. The tubular member 40 further includes a first solution delivery port 44 and a second solution delivery port 46. Both ports extend along the longitudinal axis of the tubular body from a proximal end 48 to a distal end 50 thereof. Each port 44, 46 is coupled to a syringe 52 at the proximal end thereof so as to define delivery structure. The syringes facilitate delivery of first and second solutions 23, 25 through the appropriate ports (FIG. 1). Each distal end of ports 44 and 46 opens into a mixing reservoir 54 at the distal end 50 of the tubular member, so that solution disposed in ports 44 and 46 can intermix therein. The distal end includes a disc-shaped porous member 56 coupled to the tubular member. The porous member 56 is an open pore structure, having sponge-like characteristic, yet is firm. The porous member has a curved end and aids in preventing the material 22, delivered to the puncture, to be deposited through the puncture and into the lumen. As an alternative to the porous member, a screen member, perforated blunt tip or the like may be employed.

Proximal to the distal end 50 is a low pressure balloon 58. The balloon 58 is affixed to the body 40 by threads or the like. The balloon 58 is made of material similar to that of the elongate body 40, which may be inflated into a wedge shape with its widest base facing the distal end of the catheter. Alternatively, the balloon may be inflated into a corrugated shape or the like. The inflated balloon 58 serves to exert lateral pressure against the surrounding subcutaneous tissue 32 (FIG. 3) and by so doing, secures the distal end 50 against the puncture site, with the thrombogenic, hemostatic material therebetween, providing direct mechanical and chemical hemostasis, as will become more apparent below.

A passage 60 extending the longitudinal axis of the body 40 is provided for inflating the balloon 58. The passage 60 connects with tube 62, which in turn is attached to inflating syringe 64. A stopcock 66 is provided to regulate the inflation of the balloon 58.

A second embodiment of the device 10 is shown in FIG. 5. The device 10 is similar in many respects to that of the first embodiment. Accordingly, corresponding part numbers are assigned the same reference numbers and will not be specifically described. In this embodiment, instead of providing the guide wire port 42, the first solution port 44 and the second solution port 46 are integral parts of the tubular member 40, these ports are provided within a separate plunger member 70. The plunger member 70 is slidable within the tubular member 40. Ports 44, 46 are open at the distal end 50 of the plunger member. Proximal ends of ports 44, 46 are coupled to respective syringes 52. Porous member 56 is coupled to distal end 50 so as to define a reservoir 54 therebetween, which enables solutions disposed in respective ports 44, 46 to intermix.

The procedure for percutaneous sealing of the puncture site will be explained with reference to FIGS. 2-4. As noted above, it can be appreciated that various methods of delivering the thrombogenic, hemostatic material to the puncture may be employed. For example, a tube may be employed which leads to the puncture, as in European Patent Application No. 476,178A1. The thrombogenic, hemostatic material may then be delivered through the tube to the puncture, without use of a guide member, to promote clotting at the puncture. However, it is preferable to deliver the material to the puncture while a guide wire is disposed in the puncture to ensure that the material is accurately delivered to the puncture.

Figure 2:
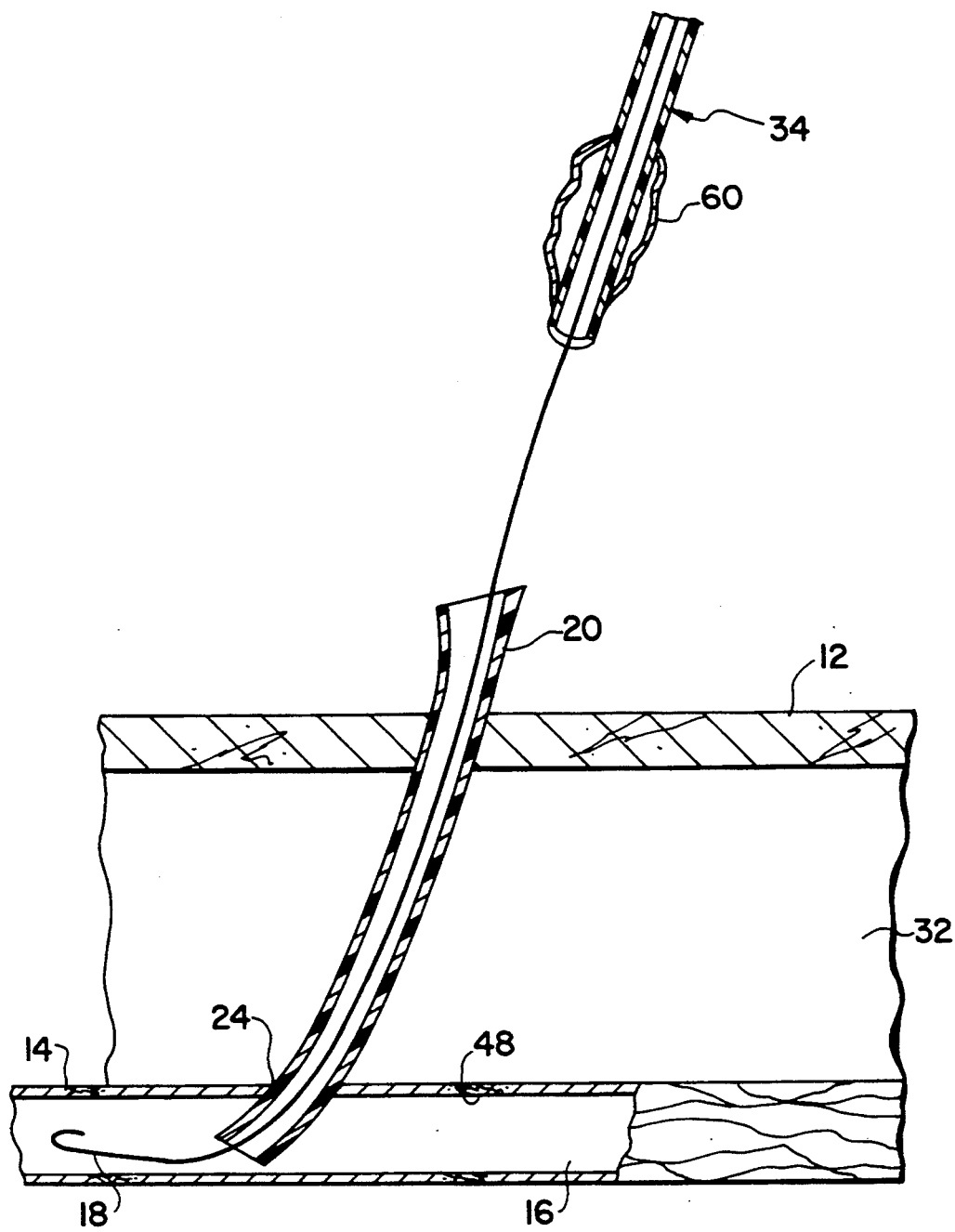
FIG. 2 is a side elevational view in partial section of a portion of the hemostatic device of FIG. 1, about to be inserted into a conventional arterial sheath extending through a percutaneous puncture into the arterial lumen, the device being shown with solution delivery ports removed for clarity.
Figure 3:
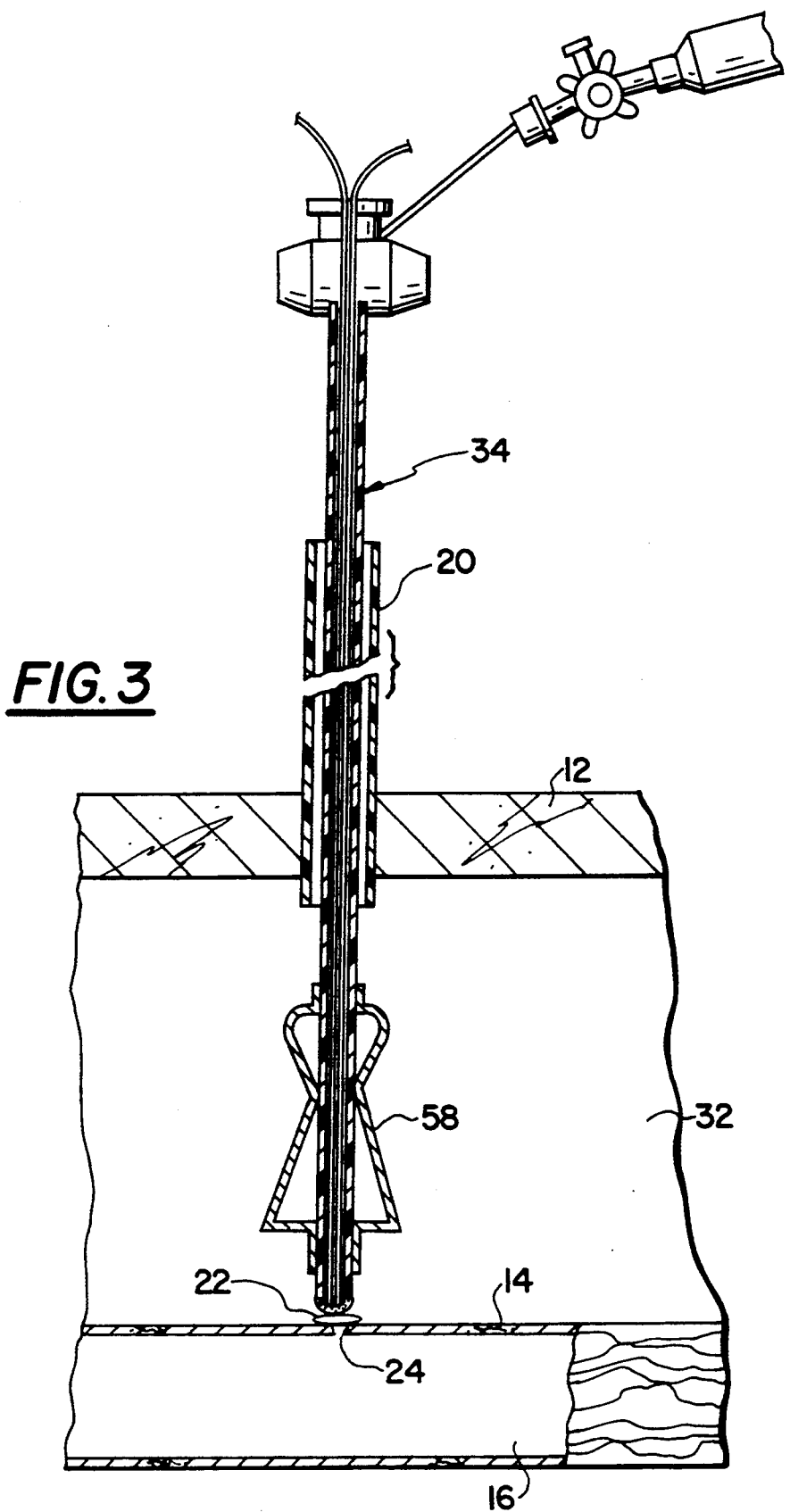
FIG. 3 is a side elevational view in partial section of the hemostatic device of FIG. 1, shown in position enabling a thrombogenic, hemostatic material to precipitate formation of a clot at the puncture in a vessel to seal the puncture, with the guide wire removed.

Thus, in accordance with the invention, once the catheterization or intravascular procedure is completed, and preferably with the sheath 20 remaining in place, the guide wire 18 is re-advanced through the arterial sheath 20 into the arterial lumen 16 (FIG. 2). The arterial sheath 20 is retracted from the arterial lumen 16 (FIG. 3) as the device 10 is advanced over the guide wire 18 and through the sheath 20 until the device 10 approaches the puncture orifice 24. Brief manual compression of the artery 14 may be used to stop blood flow during retraction of the arterial sheath 20.

While advancing the device 10 over the guide wire 18, two solutions are instilled in respective solution ports 44, 46, which in combination produce fibrin glue. As stated above, one solution 23 most preferably comprises a mixture of sodium citrate and autologous patient blood, and is disposed in port 44. The second solution 25 most preferably comprises a mixture of bovine thrombin in water and aminocaproic acid is disposed in port 46. As stated above, both solutions are in liquid form so as to easily flow through the delivery catheter 34 to the distal end thereof and intermix to form the thrombogenic, hemostatic material 22 in the reservoir 54. When the distal end of the delivery catheter is disposed at the puncture site, the material 22, which is being forced through the porous member due to the pressure created by syringes 52, contacts the wall of the artery, promoting clotting and thus, sealing the puncture. The porous member 56 ensures that the material 22 is deposited on the exterior wall of the artery and delivered into the artery through the puncture. The material 22 has a gel-like consistency enabling it to substantially remain where it has been deposited. Referring to FIG. 4, it can be seen that the puncture tends to close once the cardiovascular devices are removed therefrom. The material 22 is deposited over, and remains at, the puncture site to promote clotting.

From the foregoing, it can be appreciated that the invention provides chemical hemostasis of the puncture. Further, once the distal end 50 of the tubular member is felt to be against the arterial puncture site, which is perceived as resistance to further advancement and lack of bleeding when pressure exerted on the proximal part of the artery is released transiently, the balloon 58 is inflated using the inflation syringe 64. Inflation of the balloon secures the porous member of the distal end 50 against the puncture site. Thereafter, manual pressure on the artery 14 is released. The guide wire 18 is then withdrawn from the artery 14 and from the hemostatic catheter 34 respectively. Thus, the device 10 maintains mechanical and chemical hemostatic pressure directly to the arterial puncture site 24, as shown in FIG. 3, without the need for prolonged manual arterial compression. The inflated balloon 58 remains at the puncture site and will permit full patient ambulation while the hemostatic device 10 remains in place. Once hemostasis is achieved due to clot formation, the balloon is deflated and the hemostatic device and arterial sheath are removed from the patient. FIG. 4 show the thrombogenic, hemostatic material 22 applied to the puncture 22 to as to promote sealing thereof, after the hemostatic device and arterial sheath are removed.

The device of the second embodiment also permits the two solutions to be mixed at the distal end to form the material 22. Once the device is felt to be at the puncture site, the plunger member 70 is advanced, so that the porous member 56 is near or in contact with the wall of the artery. The thrombogenic, hemostatic material 22 is then passed through the porous member to contact the punctured wall of the artery to promote clotting. Thereafter, inflation of the balloon 58 secures the device to the puncture site.

It can be appreciated that each embodiment of the device of the invention provides both chemical and mechanical hemostasis at the puncture site. It can also be appreciated that the thrombogenic, hemostatic material 22 can be comprised of blood from the patient, which eliminates health risks associated with utilizing donor blood to form the material 22. Further, if desired, a high viscosity bio-absorbable hemostatic gel, glue or desiccated gelatin such as gelfoam may be applied to the distal end of the delivery catheter 34 prior to delivering the material 22 to the puncture site to strengthen the material and aid in promoting clotting and thus sealing of the puncture site 24.

It is preferable to deliver the material 22 to the puncture site under the least amount of pressure possible. Therefore, it is most preferable to mix the two solutions at the puncture site, since it is easy to deliver two low viscosity fluids to the puncture site and thereafter intermix to form a higher viscosity material 22, than it is to deliver a high viscosity fluid directly to the puncture. Of course, if desired, the thrombogenic, hemostatic material 22 can be delivered directly to the puncture.

As stated above, it is preferable to retract the arterial sheath 20 from the puncture without completely removing it from the patient's body prior to threading the delivery catheter 34 over the guide wire 18, since the sheath 20 provides an unobstructed delivery channel for the delivery catheter 34 to pass therethrough to reach the puncture site. However, it can be appreciated that arterial sheath can be completely removed from the body. When using a guide wire, the guide wire 18 can then be reintroduced into the puncture site prior to removing the final catheter required for the procedure. The final catheter may then be removed. With the guide wire in place, the delivery catheter 34 may then be threaded thereon and moved to the puncture site to deliver the thrombogenic, hemostatic material 22 to the puncture site.

It can be appreciated that the method of the present invention provides hemostatic closure of a puncture or other opening in other types of ducts or lumens within the body without obstructing blood flow, since the thrombogenic, hemostatic material is delivered to an exterior wall of the artery at the puncture, without entering the lumen.

Thus, it is to be understood that while the description of the invention as contained herein is directed to closing off percutaneous punctures in arteries, the device and method have wide-spread applications. It can be appreciated by those skilled in the art, that while the invention may have primary utility for the percutaneous hemostatic closure of arterial punctures following percutaneous transluminal intravascular procedures, the invention also facilitates percutaneous closure of punctures or openings in any organ, wall or tissue plane separating separate lumens or cavities in a living being.

It has thus been seen that the objects of this invention have been fully and effectively accomplished. It will be realized, however, that the foregoing preferred embodiments have been shown and described for the purposes of illustrating the structural and functional principles of the present invention, as well as illustrating the method of employing the preferred embodiments and are subject to change without departing from such principles. Therefore, this invention includes all modifications encompassed within the spirit of the following claims.

I claim:

1. A method of closing a puncture in a wall of an artery, the method comprising the steps of:
   extending a removable guide wire into a passage leading to the puncture so that a distal end of the guide wire is disposed within the artery and a proximal end of the guide wire extends through the puncture,
   moving an elongated cardiovascular catheter over the guide wire and into the artery,
   withdrawing the cardiovascular catheter from the artery leaving the guide wire extending through the puncture,
   introducing a thrombogenic, hemostatic material over the guide wire so as to contact the artery at the puncture enabling the material to precipitate clot formation and seal the puncture, and
   withdrawing the guide wire from the puncture leaving the puncture sealed by a precipitated clot.

2. The method as claimed in claim 1, wherein the step of introducing the thrombogenic, hemostatic material to the puncture includes moving a delivery catheter inwardly over the guide wire toward the puncture, said material being provided at a distal end of said delivery catheter.

3. The method as claimed in claim 2, further including providing a balloon near the distal end of said delivery catheter, the method further comprising the step of inflating said balloon after introducing the thrombogenic, hemostatic material at the puncture, said balloon exerting lateral pressure against subcutaneous tissue so as to hold said distal end of the delivery catheter in a sealed, blocking relation with said puncture.

4. The method as claimed in claim 1, wherein the step of introducing the thrombogenic, hemostatic material to the puncture includes providing two solutions, said solutions having viscosities such that each solution may flow separately to the puncture and thereafter intermix at the puncture to form said thrombogenic, hemostatic material, said material contacting a puncture location and having a viscosity such that it substantially remains in place at the puncture location.

5. The method as claimed in claim 1, wherein said step of introducing said thrombogenic, hemostatic material includes providing a biocompatible and bioabsorbable fibrin glue material.

6. The method as claimed in claim 5, wherein a component of said fibrin glue material is selected from the group consisting of gelatin and a blood component.

7. The method as claimed in claim 6, wherein said blood component is selected from the group consisting of collagen, blood coagulation factors, blood proteins, fibrinogen, fibrin, thrombin, epsilon aminocaproic acid, autologous blood clots and subcutaneous tissue.

8. A method of closing a puncture in a wall of an artery, the method comprising the steps of:
   extending an exterior guide member through a passage leading to the puncture and through the puncture in the wall of the artery and into the artery,
   guidingly moving an elongated cardiovascular catheter through the guide member into the artery,
   withdrawing the cardiovascular catheter from the guide member,
   extending a delivery catheter into said guide member,
   moving the guide member outwardly so that it no longer extends within the puncture,
   providing a thrombogenic, hemostatic material at a distal end of the delivery catheter, and
   moving the delivery catheter inwardly so that the thrombogenic, hemostatic material contacts the artery at the puncture site enabling the material to precipitate clot formation and seal said puncture.

9. A method of closing a puncture in a wall of an artery, the method comprising the steps of:
   extending an exterior guide tube through a passage leading to the puncture and through the puncture in the wall of the artery and into the artery,
   guidingly moving an elongated cardiovascular catheter through the guide tube into the artery,
   withdrawing the cardiovascular catheter from the guide tube,
   extending a removable guide wire through the guide tube into the artery so that a distal end of the guide wire is disposed within the artery and a proximal portion of the guide wire extends through the puncture,
   moving a delivery catheter over the guide wire and threading the guide wire longitudinally through the delivery catheter,
   extending the delivery catheter into said guide tube so that the guide wire extends from the delivery catheter through said puncture,
   moving the guide tube outwardly so that it no longer extends within the puncture and leaves the guide wire extending through the puncture,
   providing a thrombogenic, hemostatic material at a distal end of the delivery catheter,
   moving the delivery catheter inwardly along the guide wire so that the guide wire guides the distal end to the puncture permitting the thrombogenic, hemostatic material to contact the artery at the puncture site enabling the material to precipitate clot formation and seal said puncture, and withdrawing the guide wire from the puncture leaving the puncture sealed by a precipitated clot.

10. The method as claimed in claim 9, further including the step of inflating a balloon after moving the delivery catheter inwardly along the guide wire so that the material contacts the artery at the puncture site, said balloon exerting lateral pressure against subcutaneous tissue so as to hold said distal end of the delivery catheter in blocking relation with said puncture.

11. A device for closing a puncture in a wall of an artery comprising:

an elongated member having a distal end, said elongated member sized to be fitted through a passageway leading to said puncture so that said distal end is disposed near said puncture in said artery, and means for delivering a thrombogenic, hemostatic material through said elongated member to said distal end thereof, said material precipitating formation of a clot upon contact with the artery at said puncture to seal said puncture, said delivering means including:

first and second delivery ports extending longitudinally through said elongated member, each said first and second port being adapted to direct respective first and second solutions to said distal end, and a mixing reservoir disposed at said distal end, said solutions mixing in said reservoir and forming said thrombogenic, hemostatic material.

12. A device as claimed in claim 11, in combination with a guide tube, said guide tube being constructed and arranged to extend through an adjacent skin area through the body containing the artery, through the puncture in the wall of the artery and into the artery to enable a cardiovascular catheter to be guidingly moved through said guide tube and into the artery, said guide tube and cardiovascular catheter being removed from the puncture and said Cardiovascular catheter being removed from said guide tube enabling said guide tube to receive said elongated member enabling said elongated member to be guidingly moved therethrough so as to deliver said thrombogenic, hemostatic material to said puncture.

13. A device as claimed in claim 11, wherein said first and second solutions have viscosities such that each said solution may flow to said distal end and thereafter intermix in said mixing reservoir to form said material, said material having a viscosity such that it substantially remains in place at said puncture.

14. A device as claimed in claim 11, wherein said delivering means further includes first and second syringes for directing said first and second solutions to said delivery ports.

15. The device as claimed in claim 11, wherein said thrombogenic, hemostatic material is a biocompatible and bioabsorbable fibrin glue.

16. The device as claimed in claim 11, wherein a component of said thrombogenic, hemostatic material is selected from the group consisting of gelatin and a blood component.

17. The device as claimed in claim 16, wherein said blood component is selected from the group consisting of collagen, blood coagulation factors, blood proteins, fibrinogen, fibrin, thrombin, epsilon aminocaproic acid, autologous blood clots and subcutaneous tissue.

18. A device as claimed in claim 11, further comprising an inflatable balloon disposed about a lower peripheral portion of said elongated member, said balloon being inflated so as to stably hold said distal end of said elongated member against said puncture.

19. A device as claimed in claim 18, wherein said elongated member further includes means for inflating said balloon.

20. A device for closing a puncture in a wall of an artery comprising:

an elongated member having a distal end, said elongated member sized to be fitted through a passageway leading to said puncture so that said distal end is disposed near said puncture in said artery, and means for delivering a thrombogenic, hemostatic material through said elongated member to said distal end thereof, said material precipitating formation of a clot upon contact with the artery at said puncture to seal said puncture, said delivering means including:

a plunger member extending longitudinally through said elongated member, said plunger member having first and second delivery ports extending longitudinally therethrough, each said first and second port being adapted to direct respective first and second solutions to the distal end of the elongated member, and a mixing reservoir defined at said distal end of said plunger member, said solutions mixing in said reservoir and forming said material, said plunger member being movable within said elongated member so that said material can be expelled from said distal end of said plunger member to said puncture to promote clotting at said puncture.

21. A device as claimed in claim 20, wherein said delivering means further includes first and second syringes for directing said first and second solutions to said delivery ports.

22. A device as claimed in claim 20, further comprising an inflatable balloon disposed about a lower peripheral portion of said elongated member, said balloon being inflated so as to stably hold said distal end of said elongated member against said puncture.

23. A device as claimed in claim 22, wherein said elongated member further includes means for inflating said balloon.

24. A device for closing a puncture in a wall of an artery comprising:

an elongated member having a distal end, said elongated member sized to be fitted through a passageway leading to said puncture so that said distal end is disposed near said puncture in said artery, and means constructed and arranged with respect to the elongated member for delivering a thrombogenic, hemostatic material through said elongated member to said distal end, said material precipitating formation of a clot upon contact with the artery at said puncture to seal said puncture, said distal end including a disk-shaped porous member constructed and arranged to permit said material to pass therethrough and contact the artery at the puncture without being introduced into the artery, said porous member including a surface constructed and arranged to provide pressure against the puncture site to promote mechanical hemostasis while holding said material against the puncture site to facilitate rapid biological hemostasis.

25. A device as claimed in claim 24, further comprising an inflatable balloon disposed about a lower peripheral portion of said elongated member, said balloon being inflated so as to stably hold said distal end of said elongated member against said puncture.

26. A device as claimed in claim 25, wherein said elongated member further includes means for inflating said balloon.

27. A device a puncture in a wall of an artery comprising:
   an elongated member having a distal end, said elongated member sized to be fitted through a passageway leading to said puncture so that said distal end is disposed near said puncture in said artery,
   movable guide means for extension through said puncture, an end thereof being threaded longitudinally through said elongated member for guiding said distal end of said elongated member to said puncture,
   a thrombogenic, hemostatic material,
   means constructed and arranged with respect to the elongated member for delivering said thrombogenic, hemostatic material through said elongated member to said distal end thereof, said material precipitating formation of a clot upon contact with the artery at said puncture to seal the puncture, and
   means coupled to said distal end of said elongated member for exerting pressure on subcutaneous tissue near said passageway so as to stably hold said thrombogenic, hemostatic material against said puncture.

28. A device as claimed in claim 27, wherein said exerting means comprises an inflatable balloon disposed about a lower peripheral portion of said elongated member, said balloon being inflated so as to stably hold said distal end against said puncture.

29. A device for closing a puncture in a wall of an artery comprising:
   an elongated member having a distal end, said elongated member sized to be fitted through a passageway leading to said puncture so that said distal end is disposed near said puncture in said artery,
   movable guide means extending longitudinally through said elongated member for extension through said puncture for guiding said distal end to said puncture, and
   means constructed and arranged with respect to the elongated member for delivering a thrombogenic hemostatic material through said elongated member to said distal end, said material precipitating formation of a clot upon contact with the artery at said puncture to seal said puncture.

30. A device as claimed in claim 29, wherein said movable guide means is a guide wire.

31. A method of closing a puncture in a wall of an artery, the method comprising the steps of:
   moving an elongated cardiovascular catheter through the puncture into the artery for treatment of the artery,
   withdrawing the cardiovascular catheter from the artery upon completion of arterial treatment, and
   introducing a thrombogenic, hemostatic material to the puncture so as to contact the artery at the puncture enabling the material to precipitate clot formation and seal the puncture, said thrombogenic, hemostatic material being formed from a mixture of two solutions, said solutions having viscosities such that each solution may flow separately to the puncture and thereafter intermix at the puncture to form said material, said material contacting a puncture location and having a viscosity such that it substantially remains in place at the puncture location.

32. A device a puncture in a wall of an artery comprising:
   an elongated member having a distal end, said elongated member sized to be fitted through a passageway leading to said puncture so that said distal end is disposed near said puncture in said artery,
   a thrombogenic, hemostatic material, and
   at least one delivery port extending within said elongated member and constructed and arranged to deliver said thrombogenic, hemostatic material through said elongated member to said distal end thereof, said material precipitating formation of a clot upon contact with the artery at said puncture to seal said puncture,
   said delivery structure including:
   first and second delivery ports extending longitudinally through said elongated member, each said first and second port being adapted to direct respective first and second solutions to said distal end, and
   a mixing reservoir disposed at said distal end, said solutions mixing in said reservoir and forming said thrombogenic, hemostatic material.

33. A device as claimed in claim 32, wherein said first and second solutions have viscosities such that each said solution may flow to said distal end and thereafter intermix in said mixing reservoir to form said material, said material having a viscosity such that it substantially remains in place at said puncture.

34. A device as claimed in claim 32, wherein said delivery structure further includes first and second syringes for directing said first and second solutions to said delivery ports.

35. The device as claimed in claim 32, wherein said thrombogenic, hemostatic material is a biocompatible and bioabsorbable fibrin glue.

36. The device as claimed in claim 32, wherein a component of said thrombogenic, hemostatic material is selected from the group consisting of gelatin and a blood component.

37. The device as claimed in claim 36, wherein said blood component is selected from the group consisting of collagen, blood coagulation factors, blood proteins, fibrinogen, fibrin, thrombin, epsilon aminocaproic acid, autologous blood clots and subcutaneous tissue.

38. A device as claimed in claim 32, further comprising an inflatable balloon disposed about a lower peripheral portion of said elongated member, said balloon being inflated so as to stably hold said distal end of said elongated member against said puncture.

39. A device for closing a puncture in a wall of an artery comprising:
   an elongated member having a distal end, said elongated member sized to be fitted through a passageway leading to said puncture so that said distal end is disposed near said puncture in said artery, and
   delivery structure constructed and arranged to deliver a thrombogenic, hemostatic material through said elongated member to said distal end thereof, said material precipitating formation of a clot upon contact with the artery at said puncture to seal said puncture,
   said delivery structure including:

a plunger member extending longitudinally through said elongated member, said plunger member having first and second delivery ports extending longitudinally therethrough, each said first and second port being adapted to direct respective first and second solutions to the distal end of the elongated member, and a mixing reservoir defined at said distal end of said plunger member, said solutions mixing in said reservoir and forming said material, said plunger member being movable within said elongated member so that said material can be expelled from said distal end of said plunger member to said puncture to promote clotting at said puncture.

40. A device as claimed in claim 39, wherein said delivery structure further includes first and second syringes for directing said first and second solutions to said delivery ports.

41. A device as claimed in claim 39, further comprising an inflatable balloon disposed about a lower peripheral portion of said elongated member, said balloon being inflated so as to stably hold said distal end of said elongated member against said puncture.

42. A device for closing a puncture in a wall of an artery comprising:

an elongated member having a distal end, said elongated member sized to be fitted through a passageway leading to said puncture so that said distal end is disposed near said puncture in said artery, a thrombogenic, hemostatic material, and at least one delivery port extending within said elongated member and constructed and arranged to deliver said thrombogenic, hemostatic material through said elongated member to said distal end, said material precipitating formation of a clot upon contact with the artery at said puncture to seal said puncture, said distal end including a porous member disposed at said distal end so as to permit said material to pass therethrough and contact the artery at the puncture without being introduced into the artery, said porous member including a surface constructed and arranged to provide pressure against the puncture site to promote mechanical hemostasis while holding said material against the puncture site to facilitate rapid biological hemostasis.

43. A device as claimed in claim 42, further comprising an inflatable balloon disposed about a lower peripheral portion of said elongated member, said balloon being inflated so as to stably hold said distal end of said elongated member against said puncture.

44. A device for closing a puncture in a wall of an artery comprising:

an elongated member having a distal end, said elongated member sized to be fitted through a passageway leading to said puncture so that said distal end is disposed near said puncture in said artery, a movable guide wire constructed and arranged to extend through said puncture, an end thereof being threaded longitudinally through said elongated member for guiding said distal end of said elongated member to said puncture, a thrombogenic, hemostatic material, at least one delivery port extending within said elongated member and constructed and arranged to deliver said thrombogenic, hemostatic material through said elongated member to said distal end thereof, said material precipitating formation of a clot upon contact with the artery at said puncture to seal the puncture, and an inflatable balloon coupled to said distal end of said elongated member constructed and arranged to exert pressure, upon inflation thereof, on subcutaneous tissue near said passageway so as to stably hold said thrombogenic, hemostatic material against said puncture.

45. A device as claimed in claim 44, wherein said inflatable balloon is disposed about a lower peripheral portion of said elongated member.

46. A device for closing a puncture in a wall of an artery comprising:

an elongated member having a distal end, said elongated member sized to be fitted through a passageway leading to said puncture so that said distal end is disposed near said puncture in said artery, a movable guide wire constructed and arranged to extend longitudinally through said elongated member and extend through said puncture for guiding said distal end to said puncture, a thrombogenic, hemostatic material, and at least one delivery port extending within said elongated member and constructed and arranged to deliver said thrombogenic, hemostatic material through said elongated member to said distal end, said material precipitating formation of a clot upon contact with the artery at said puncture to seal said puncture.

* * * * *